United States Patent
Ozawa et al.

(10) Patent No.: US 7,906,631 B2
(45) Date of Patent: Mar. 15, 2011

(54) METHOD OF PRODUCING RARE EARTH SALT OF DIALKYL PHOSPHATE OR DIOLEYL PHOSPHATE

(75) Inventors: Yoichi Ozawa, Kodaira (JP); Hideaki Suzuki, Odawara (JP)

(73) Assignee: Bridgestone Corporation, Tokyo (JP)

( * ) Notice: Subject to any disclaimer, the term of this patent is extended or adjusted under 35 U.S.C. 154(b) by 0 days.

(21) Appl. No.: 12/682,866

(22) PCT Filed: Oct. 15, 2008

(86) PCT No.: PCT/JP2008/068682
§ 371 (c)(1),
(2), (4) Date: Apr. 13, 2010

(87) PCT Pub. No.: WO2009/051144
PCT Pub. Date: Apr. 23, 2009

(65) Prior Publication Data
US 2010/0228044 A1    Sep. 9, 2010

(30) Foreign Application Priority Data

Oct. 15, 2007  (JP) ................................. 2007-267991

(51) Int. Cl.
*C07F 5/00*  (2006.01)
(52) U.S. Cl. .......................................... 534/15; 556/24
(58) Field of Classification Search ..................... 534/15; 556/24
See application file for complete search history.

(56) References Cited

U.S. PATENT DOCUMENTS

| 4,931,376 A | 6/1990 | Ikematsu et al. |
| 6,767,927 B1 * | 7/2004 | Yunlu et al. ..................... 516/33 |

FOREIGN PATENT DOCUMENTS

| JP | 61-019611 A | 1/1986 |
| JP | 61-097311 A | 5/1986 |
| JP | 11-255813 A | 9/1999 |
| JP | 2000-247986 A | 9/2000 |
| JP | 2002-543083 A | 12/2002 |
| JP | 2003-081983 A | 3/2003 |

* cited by examiner

*Primary Examiner* — Porfirio Nazario Gonzalez
(74) *Attorney, Agent, or Firm* — Sughrue Mion, PLLC

(57) ABSTRACT

There is provided a method of producing a rare earth salt of a dialkyl phosphate or a rare earth salt of dioleyl phosphate of a high purity useful as a polymerization catalyst of a conjugated diene compound by directly reacting a rare earth oxide or a rare earth hydroxide with a dialkyl phosphate or dioleyl phosphate of a high purity. In the invention, the rare earth oxide or rare earth hydroxide is reacted with the dialkyl phosphate or dioleyl phosphate of a high purity in a non-polar solvent in the presence of at least one compound selected from a halogenated hydroacid, phosphorous acid and a rare earth halide made from the same element as in an objective product as a catalyst.

18 Claims, No Drawings

METHOD OF PRODUCING RARE EARTH SALT OF DIALKYL PHOSPHATE OR DIOLEYL PHOSPHATE

CROSS REFERENCE TO RELATED APPLICATIONS

This application is a National Stage of International Application No. PCT/JP2008/068682 filed Oct. 15, 2008, which claims priority from Japanese Patent Application No. 2007-267991, filed Oct. 15, 2007, the contents of all of which are incorporated herein by reference in their entirety.

TECHNICAL FIELD

This invention relates to a method of producing a rare earth salt of dialkyl phosphate or a rare earth salt of dioleyl phosphate, which is useful as a polymerization catalyst for conjugated diene polymers, and particularly to a method of producing a rare earth salt of dialkyl phosphate. More specifically, the invention relates to a method wherein a rare earth oxide or a rare earth hydroxide is reacted with a dialkyl phosphate of a high purity in a non-polar solvent in the presence of at least one compound selected from a halogenated hydroacid, phosphorous acid and a rare earth halide as a catalyst to produce a high purity rare earth salt of dialkyl phosphate or dioleyl phosphate, especially neodymium salt of dialkyl phosphate or a lanthanum salt of dialkyl phosphate.

RELATED ART

Conjugated diene polymers used for various applications are produced by using various polymerization reactions from various conjugated diene compounds for imparting diverse properties matched with the respective application. In the polymerization reaction of the conjugated diene compound are used a variety of catalyst systems. Particularly, a catalyst system containing a rare earth metal compound as an essential component is frequently used in the form of a composite catalyst comprising a rare earth metal compound, an organometallic compound and a halide, and has a characteristic that polymers having different properties can be produced by variously changing the kind and amount of the organometallic compound such as an organoaluminum compound, an organomagnesium compound or the like as another component in the composite catalyst. As the rare earth compound, rare earth salts of dialkyl phosphate such as lanthanum di(2-ethylhexyl) phosphate, neodymium di(2-ethylhexyl)phosphate and so on tend to be increasingly used because their catalytic activities are excellent as compared with those of the other rare earth compounds. However, if an impurity(s) is included in the rare earth salt of dialkyl phosphate or a greater amount of unreacted starting material is retained therein, the amount of the organometallic compound required when being used as the composite catalyst is increased and so on, whereby economic efficiency is damaged and the catalytic activity is lowered and further the impurities or their decomposed matters are residual in the resulting polymer using the composite catalyst, resulting in the unfavorable influence such as necessity of removing them in accordance with the production process of the polymer and the applications of the polymer, so that the rare earth salt of dialkyl phosphate or dioleyl phosphate is desired to have a higher purity. For the purpose of obtaining the rare earth salt of dialkyl phosphate in a higher purity, therefore, there is also a tendency of using a dialkyl phosphate with a high purity as a starting material. As a method of producing the rare earth salt of dialkyl phosphate are already disclosed the following methods.

(1) A technique of reacting an alkali metal salt of an organic acid with a lanthanum chloride in water or an organic solvent such as alcohol, ketone or the like to obtain an organic acid salt of lanthanum (JP-A-S61-97311).

(2) A technique wherein a solution of di-2-ethylhexyl phosphoric acid in hexane is added with an ammonia solution to obtain an aqueous solution of ammonium di-2-ethylhexyl phosphate in hexane, which is added and reacted with an aqueous solution of lanthanum nitrate and added with dipropylene glycol to obtain lanthanum tris(di-2-ethylhexyl phosphate) (JP-A-2002-543083).

(3) A technique of reacting lanthanum oxide and hydrogen bis(2-ethylhexyl) phosphate in hexane and water to obtain lanthanum tris[bis(2-ethylhexyl)phosphate] (JP-A-H11-255813).

DISCLOSURE OF THE INVENTION

When a rare earth salt of dialkyl phosphate is produced by reacting a rare earth oxide or a rare earth hydroxide with a dialkyl phosphate of a high purity, the technique (1) is required to provide an alkali metal salt of dialkyl phosphate by firstly reacting dialkyl phosphate with an alkali metal hydroxide, but a part of dialkyl phosphate is hydrolyzed by the reaction between the dialkyl phosphate and the alkali metal hydroxide to produce monoalkyl phosphate, and hence lanthanum monoalkyl phosphate is by-produced in the subsequent reaction between the alkali metal salt of dialkyl phosphate and the rare earth chloride, so that the rare earth salt of dialkyl phosphate can not be obtained in a higher purity.

Even in the technique (2), a part of dialkyl phosphate is hydrolyzed by the reaction of dialkyl phosphate with ammonia to produce monoalkyl phosphate, and the rare earth salt of monoalkyl phosphate is by-produced by the reaction of ammonium dialkyl phosphate with rare earth nitrate, so that the rare earth salt of dialkyl phosphate can not be obtained in a higher purity. In the technique (3), there is no problem on the hydrolysis of dialkyl phosphate, but when dialkyl phosphate of a high purity is used, the reaction is not completed for unknown reasons, and unreacted rare earth oxide or rare earth hydroxide and dialkyl phosphate remain. Among them, the unreacted rare earth oxide or rare earth hydroxide can be removed by filtering the reaction solution, while the unreacted dialkyl phosphate is very difficult to be removed from the reaction system and retains in the objective product, so that there is a problem that the rare earth salt of dialkyl phosphate can not be obtained in a higher purity. For this end, it is strongly desired to develop a method of producing the rare earth salt of dialkyl phosphate in a high purity.

The inventors have made examinations on a method of producing a rare earth salt of dialkyl phosphate or a rare earth salt of dioleyl phosphate in a high purity by directly reacting a rare earth oxide or a rare earth hydroxide with dialkyl phosphate or dioleyl phosphate of a high purity, and found that the rare earth oxide or rare earth hydroxide is reacted with dialkyl phosphate or dioleyl phosphate having a purity of not less than 97% and represented by the following formula (1):

[in the formula (1), R is an alkyl group having a carbon number of 1 to 18 or oleyl group] in a non-polar solvent in the presence of at least one compound selected from a halogenated hydroacid, phosphorous acid and a lanthanum halide as a catalyst, whereby the reaction is rapidly progressed to suppress retaining of unreacted rare earth oxide or rare earth hydroxide and dialkyl phosphate or dioleyl phosphate and also a rare earth salt of dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group], and as a result, the invention has been accomplished.

According to the production method of the invention, the rare earth salt of dialkyl phosphate or rare earth salt of dioleyl phosphate, which is useful as a polymerization catalyst of a conjugated diene compound, particularly lanthanum dialkyl phosphate can be produced in a higher purity.

BEST MODE FOR CARRYING OUT THE INVENTION

The invention will be described in detail below.

The invention provides a method of producing a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group], characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of at least one compound selected from a halogenated hydroacid, phosphorous acid and a lanthanum halide as a catalyst.

As the rare earth element are preferable neodymium, lanthanum, scandium, yttrium, samarium and gadolinium, and neodymium and lanthanum are more preferable, and particularly lanthanum is preferable. Moreover, the rare earth means elements including scandium element and lanthanoid except actinoid. These elements are very similar to each other in the chemical properties and develop the same effects, so that they are possible to be used in the object of the invention. Particularly, neodymium, lanthanum, scandium, yttrium, samarium and gadolinium are known to impart an activity useful as a polymerization catalyst, and are preferable as a starting material in the production method of the invention because rare earth oxide ($M_2O_3$ type) or rare earth hydroxide ($M(OH)_3$ type), in which oxidation number of the rare earth element is 3, and a hydrate thereof are existent stably and easy in industrial availability. Especially, neodymium and lanthanum are preferable because the utility as a polymerization catalyst is excellent. Moreover, when these rare earth compounds are used as a polymerization catalyst, they may provide characteristics on different polymerization reactions (activity, microstructure of resulting polymer, and so on), but they are equal in the synthesis reaction of the rare earth salt of dialkyl phosphate or rare earth salt of dioleyl phosphate handled with in the scope of the invention. Moreover, lanthanum is mentioned as a typical example to the extent possible in the description of the following best mode, and the explanation will be conducted based thereon.

As a starting material of the rare earth compound used in the invention are mentioned rare earth oxides and rare earth hydroxides, preferably lanthanum oxide [$La_2O_3$], lanthanum hydroxide [$La(OH)_3$], neodymium oxide [$Nd_2O_3$], neodymium hydroxide [$Nd(OH)_3$], scandium oxide [$Sc_2O_3$], scandium hydroxide [$Sc(OH)_3$], yttrium oxide [$Y_2O_3$], yttrium hydroxide [$Y(OH)_3$], samarium oxide [$Sm_2O_3$], samarium hydroxide [$Sm(OH)_3$], gadolinium oxide [$Gd_2O_3$] and gadolinium hydroxide [$Gd(OH)_3$], and particularly lanthanum oxide [$La_2O_3$], lanthanum hydroxide [$La(OH)_3$], neodymium oxide [$Nd_2O_3$] and neodymium hydroxide [$Nd(OH)_3$] are preferable. In general, they may be used as commercially available ones such as reagents, industrial products and so on. Also, the hydroxides may or may not contain water of crystallization as a hydrate, but the hydrates are usually preferable because they are easily available.

The dialkyl phosphate or dioleyl phosphate used in the invention is represented by the following formula (1):

$$HOPO(OR)_2 \qquad (1)$$

[in the formula (1), R is an alkyl group having a carbon number of 1 to 18 or oleyl group]. As an example of the alkyl group having a carbon number of 1 to 18 as R in the formula (1) may be mentioned methyl, butyl, 2-ethylhexyl, isodecyl, lauryl, stearyl and so on, and 2-ethylhexyl is preferable.

As a concrete example of the dialkyl phosphate used in the invention may be mentioned dimethyl phosphate, dibutyl phosphate, di(2-ethylhexyl) phosphate, diisodecyl phosphate, dilauryl phosphate, distearyl phosphate, dioleyl phosphate and so on, but di(2-ethylhexyl) phosphate is preferable because it is easily available as a reagent or an industrial product. Also, these dialkyl phosphates or dioleyl phosphate may be used alone or in a combination of two or more.

Since the dialkyl phosphate or dioleyl phosphate is a partial esterified product between phosphoric acid and an alcohol, a small amount of monoalkyl phosphate, phosphoric acid and alcohol is frequently included as an impurity. In the invention, a dialkyl phosphate having a small amount of monoalkyl phosphate and a high purity is used for obtaining lanthanum dialkyl phosphate of a high purity. The content of dialkyl phosphate is not less than 97 mass %, preferably not less than 98 mass %. When the content of dialkyl phosphate is less than 97 mass %, a great amount of monoalkyl phosphate becomes included in the starting material, and hence the monoalkyl phosphate can not be removed after the reaction with lanthanum oxide or lanthanum hydroxide and is left in the objective product, or it is reacted with lanthanum oxide or lanthanum hydroxide to by-produce lanthanum monoalkyl phosphate, so that lanthanum dialkyl phosphate can not be obtained in a high purity. Moreover, the content of monoalkyl phosphate is preferably less than 2 mass %, more preferably less than 1 mass %. When the content of monoalkyl phosphate is not less than 2 mass %, the monoalkyl phosphate can not be removed after the reaction with lanthanum oxide or lanthanum hydroxide and is left in the objective product, or it is reacted with lanthanum oxide or lanthanum hydroxide to by-produce lanthanum monoalkyl phosphate, so that lanthanum dialkyl phosphate can not be obtained in a high purity. Moreover, commercially available dialkyl phosphates as a reagent or an industrial product can be used as long as the content of monoalkyl phosphate is less and the purity is high.

The amount of the dialkyl phosphate used in the invention is 3-3.06 mol times (1-1.02 equivalent), preferably 3-3.03 mol times (1-1.01 equivalent), more preferably 3 mol times (1 equivalent) per 1 mol of lanthanum atom in lanthanum oxide or lanthanum hydroxide. Even when the dialkyl phosphate equivalent to lanthanum atom is reacted in the invention, the reaction proceeds rapidly and lanthanum dialkyl phosphate is obtained in a higher purity. When the amount of the dialkyl phosphate used is less than 3 mol times, lanthanum oxide or lanthanum hydroxide retains in the reaction solution and should be removed by filtration, and hence the number of production steps is unfavorably increased. When it exceeds 3.06 mol times, the reaction proceeds, but a great amount of unreacted dialkyl phosphate retains and is difficult to be removed from the objective product, and hence lanthanum dialkyl phosphate of a high purity is not obtained.

The compound used as a catalyst in the invention is a halogenated hydroacid, phosphorous acid and a rare earth halide made from the rare earth element same as or different from the objective product, preferably a rare earth halide made from the same rare earth element in the objective product, more preferably a rare earth halide in which the halogen is chlorine. The halogenated hydroacid is not limited, but includes hydrochloric acid, hydrobromic acid and hydroiodic acid, and hydrochloric acid is preferable. The rare earth halide may include, but is not limited to, the following compounds such as lanthanum chloride [$LaCl_3$], lanthanum bromide [$LaBr_3$], lanthanum iodide [$LaI_3$], neodymium chloride [$NdCl_3$], neodymium bromide [$NdBr_3$], neodymium iodide [$NdI_3$], scandium chloride [$ScCl_3$], scandium bromide [$ScBr_3$], scandium iodide [$ScI_3$], yttrium chloride [$YCl_3$], yttrium bromide [$YBr_3$], yttrium iodide [$YI_3$], samarium chloride [$SmCl_3$], samarium bromide [$SmBr_3$], samarium iodide [$SmI_3$], gadolinium chloride [$GdCl_3$], gadolinium bromide [$GdBr_3$] and gadolinium iodide [$GdI_3$], and among them lanthanum chloride, neodymium chloride, scandium chloride, yttrium chloride, samarium chloride and gadolinium chloride are preferable, and lanthanum chloride or neodymium chloride is more preferable. Moreover, these compounds are sufficient alone but may be used in a combination of two or more.

When the halogenated hydroacid such as hydrochloric acid, hydrobromic acid or hydroiodic acid is used in the invention, ones available as a reagent or an industrial product can be used as they are, but they may be used by diluting with water to a given concentration. Also, the halogenated hydroacid such as hydrochloric acid, hydrobromic acid or hydroiodic acid may be used by directly passing a halogenated hydrogen gas such as hydrogen chloride gas, hydrogen bromide gas or hydrogen iodide gas through water so as to adjust to a given concentration.

The concentration of hydrochloric acid used in the invention is not particularly limited, but is usually within a range of 0.3-38 mass %. Even when the concentration of hydrochloric acid is less than 0.3 mass %, if an amount required as a catalyst is added, the reaction proceeds, but a greater amount of water derived from hydrochloric acid used is existent in the reaction system, which may reduce a yield per a reaction vessel uneconomically but also a greater amount of a disposal such as waste water or the like is unfavorably generated. It is difficult to provide hydrochloric acid of more than 38 mass %.

The concentration of hydrobromic acid used in the invention is not particularly limited, but is usually within a range of 0.7-49 mass %. Even when the concentration of hydrobromic acid is less than 0.7 mass %, if an amount required as a catalyst is added, the reaction proceeds, but a greater amount of water derived from hydrobromic acid used is existent in the reaction system, which may reduce a yield per a reaction vessel uneconomically but also a greater amount of a disposal such as waste water or the like is unfavorably generated. It is difficult to provide hydrobromic acid of more than 49 mass %.

The concentration of hydroiodic acid used in the invention is not particularly limited, but is usually within a range of 1-58 mass %. Even when the concentration of hydroiodic acid is less than 1 mass %, if an amount required as a catalyst is added, the reaction proceeds, but a greater amount of water derived from hydroiodic acid used is existent in the reaction system, which may reduce a yield per a reaction vessel uneconomically but also a greater amount of a disposal such as waste water or the like is unfavorably generated. It is difficult to provide hydroiodic acid of more than 58 mass %.

In general, phosphorous acid is hardly dissolved in a non-polar solvent, so that it is difficult to disperse into the reaction system. In the invention, therefore, phosphorous acid is used in form of an aqueous solution adjusted by dissolving to a given concentration with water, but phosphorous acid may be used by adding it together with water to the reaction system. The amount of water used for dissolving phosphorous acid in the invention is a range of 0.3-120 mass times per phosphorous acid. When the amount of water used is less than 0.3 mass times, the dispersion of phosphorous acid into the non-polar solvent is difficult and the effect as a catalyst is not developed sufficiently, while when it exceeds 120 mass times, a greater amount of water is existent in the reaction system, which may reduce a yield per a reaction vessel uneconomically but also a greater amount of a disposal such as waste water or the like is unfavorably generated.

The amount of the halogenated hydroacid or phosphorous acid used as a catalyst in the invention is a range of 0.005-0.5 mol times, preferably 0.01-0.25 mol times per 1 mol of lanthanum atom in lanthanum oxide or lanthanum hydroxide. When the amount of the catalyst used is less than 0.005 mol times, the progress of the reaction becomes slow, while when it exceeds 0.5 mol times, the reaction proceeds rapidly, but the catalyst retained in the reaction solution should be removed by washing with water and hence the steps become complicated and uneconomical.

The halogenated lanthanum such as lanthanum chloride, lanthanum bromide or lanthanum iodide used as a catalyst in the invention may be an anhydrous salt or may contain water of crystallization as a hydrate, but ones containing water of crystallization are preferable because it is not required to add water to the reaction system. In case of using the anhydrous salt of the halogenated lanthanum, it is necessary that such a compound is dissolved in water or the reaction system is added with water likewise the case on phosphorous acid, and the amount of water used is a range of 0.3-120 mass times per the halogenated lanthanum. Moreover, the anhydrous salt of the rare earth chloride has drawbacks that the production is generally difficult and particularly an oxide may be necessarily and partially produced at the production step, and so on, and is difficult in the industrial availability, so that the hydrate of the rare earth chloride is preferable.

The amount of the halogenated lanthanum used as a catalyst in the invention is a range of 0.001-0.1 mol times, preferably 0.005-0.05 mol times per 1 mol of lanthanum atom in lanthanum oxide or lanthanum hydroxide. When the amount of the catalyst used is less than 0.001 mol times, the progress of the reaction becomes slow, while even when it exceeds 0.1 mol times, the reaction proceeds rapidly, but if a greater amount of the catalyst exceeding 0.1 mol times is existent in the objective product, the activity of the composite catalyst using the objective product as a polymerization catalyst of a conjugated diene compound is deteriorated, so that the catalyst retaining in the reaction solution should be removed by washing with water, and hence the steps become complicated and uneconomical.

In the reaction between lanthanum oxide or lanthanum hydroxide and the dialkyl phosphate having a purity of not less than 97%, if the reaction is conducted under a condition using no catalyst, the progress of the reaction becomes considerably slow but also the reaction is not completed though reasons are not clear, so that lanthanum oxide or lanthanum hydroxide retains in the reaction solution. When using the catalyst according to the invention, the reaction with the dialkyl phosphate having a purity of not less than 97% proceeds rapidly and is completed, and hence lanthanum dialkyl phosphate of a high purity can be obtained without leaving lanthanum oxide or lanthanum hydroxide in the reaction solution. Moreover, if a compound other than the compound according to the invention such as nitric acid, sulfuric acid, phosphoric acid usually included as an impurity in the dialkyl phosphate or the like is used in the catalyst, the reaction is not completed.

In the invention, a non-polar solvent is used as a reaction solvent. The non-polar solvent may concretely include, but is not limited to, aromatic hydrocarbons such as benzene, toluene, xylene, ethylbenzene and the like; alicyclic hydrocarbons such as methylcyclopentane, cyclohexane, methylcyclohexane and the like; and aliphatic hydrocarbons such as pentane, hexane, heptane, 2-methylpentane, 3-methylpentane, 2,3-dimethylpentane, octane and the like. From a viewpoint of handling such as solubility, volatility, adaptability to a polymerization solvent or the like, alicyclic hydrocarbon and aliphatic hydrocarbon having a carbon number of 6 or a mixture thereof are preferable, and particularly cyclohexane is preferable. Also, these non-polar solvents may be used alone or in a mixture provided that the mixing ratio may be optional.

The amount of the non-polar solvent used as a reaction solvent in the invention is usually a range of 2-20 mass times, preferably 4-10 mass times per the dialkyl phosphate. When the amount of the non-polar solvent used is less than 1.5 mass times, the dispersibility of lanthanum oxide or lanthanum hydroxide is poor and the progress of the reaction becomes slow, while when it exceeds 20 mass times, the reaction becomes slow but also the yield per the reaction vessel becomes small and uneconomical. Since the composite catalyst used in the polymerization reaction of the conjugated diene compound is frequently used in the non-polar solvent, according to the invention, the non-polar solvent is removed from the reaction solution after the completion of the reaction and, if necessary, another solvent is added for the adjustment of concentration after the removal of the solvent, whereby lanthanum dialkyl phosphate is obtained in the form of a non-polar solvent solution adjusted to a desired concentration. The concentration of lanthanum dialkyl phosphate in the solution is usually 5-50 mass %, preferably 10-40 mass %. When the concentration of lanthanum dialkyl phosphate exceeds 50 mass %, the viscosity of the solution of the lanthanum dialkyl phosphate in the non-polar solvent rises and such a solution is hardly taken out from the reaction vessel.

The reaction temperature according to the invention differs in accordance with the kind of the non-polar solvent used, but is usually a range of 0-80° C. However, if the melting point of the non-polar solvent is not lower than 0° C., the reaction is necessary to be conducted at a temperature higher than the melting point. A preferable reaction temperature is 20-70° C. When the reaction temperature is lower than 0° C., the progress of the reaction becomes considerably slow, while when it exceeds 80° C., though reasons are not clear, turbidity is caused in the reaction solution, which is difficult to confirm an end point.

The reaction time according to the invention differs in accordance with the kind and amount of the non-polar solvent used, the kind and amount of the catalyst used and the reaction temperature, but the reaction is usually terminated in 30 minutes to 3 hours.

Since the viscosity of the solution of lanthanum dialkyl phosphate in the non-polar solvent considerably rises as the concentration of lanthanum dialkyl phosphate becomes higher, according to the invention, Lewis acid may be added as a viscosity reducing agent after the completion of the reaction. As a concrete example of Lewis acid used in the invention may be mentioned a metal halide such as zinc dichloride, boron tribromide, tin tetrachloride or the like. These Lewis acids may be used alone or in a combination. When the Lewis acid is used in the invention, ones available as a reagent or an industrial product can be used as they are, or may be used by diluting with a non-polar solvent.

The amount of the Lewis acid used in the invention differs in accordance with the kind and concentration of the resulting lanthanum dialkyl phosphate and the kind and amount of the non-polar solvent used, but is usually a range of 0.005-0.5 mol times per 1 mol of lanthanum atom in lanthanum oxide or lanthanum hydroxide from a point of reducing the viscosity. When the amount of the Lewis acid is less than 0.005 mol times, the effect of reducing the viscosity is not sufficient, while when it exceeds 0.1 mol times, the activity of lanthanum dialkyl phosphate as a polymerization catalyst for the conjugated diene compound is unfavorably deteriorated. In the invention, water in the reaction solution after the completion of the reaction is removed by distilling off from the system through azeotropy with the non-polar solvent, whereas the Lewis acid may be added before or after the step of removing water, if necessary.

In the invention, the addition order of lanthanum oxide or lanthanum hydroxide as a starting material, dialkyl phosphate, catalyst and non-polar solvent is not particularly limited. The lanthanum oxide or lanthanum hydroxide, dialkyl phosphate, catalyst and non-polar solvent may be added simultaneously. In the invention, lanthanum dialkyl phosphate can be obtained by the following general method, but the invention is not limited to this method.

[General Production Method of Lanthanum Dialkyl Phosphate]

To a reaction vessel provided with an agitating apparatus and a heating-cooling apparatus are added lanthanum oxide or lanthanum hydroxide, a dialkyl phosphate, a non-polar solvent and a catalyst, which are agitated to thereby start reaction immediately and gradually raise a temperature of a reaction solution. Once the reaction solution becomes translucent, it is heated to a temperature of 50-80° C. and the reaction is further continued while maintaining this temperature. An end point of the reaction is a time point that lanthanum oxide or lanthanum hydroxide disappears and the reaction solution becomes transparent. Once the completion of the reaction is confirmed, if water layer and an organic phase are separated from each other, the reaction solution is left at rest to remove the separated water layer. Then, a reflux dehydrator is mounted onto the reaction vessel and, if necessary, Lewis acid is added thereto, and thereafter water in the reaction solution is removed by distilling off from the vessel through azeotropy with the solvent and then the solvent is distilled off to obtain a solution of lanthanum dialkyl phosphate in the non-polar solvent with a desired concentration.

The following embodiments may be mentioned in the operation of the invention.

(1) A method of producing a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group], characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of at least one compound selected from a halogenated hydroacid, phosphorous acid and a rare earth halide made from the same element as in an objective product as a catalyst.

(2) A method of producing a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group], characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of (A) 0.005-0.5 mol times of at least one compound selected from a halogenated hydroacid and phosphorous acid or (B) 0.001-0.1 mol times of at least one compound selected from rare earth halides made from the same element as in an objective product per 1 mol of a rare earth atom in the rare earth oxide or rare earth hydroxide as a catalyst.

(3) A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of at least one compound selected from a halogenated hydroacid, phosphorous acid and a lanthanum halide as a catalyst.

(4) A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of (A) 0.005-0.5 mol times of at least one compound selected from a halogenated hydroacid and phosphorous acid or (B) 0.001-0.1 mol times of at least one compound selected from rare earth halides made from the same element as in an objective product per 1 mol of a rare earth atom in the rare earth oxide or rare earth hydroxide as a catalyst.

(5) A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of (A) 0.005-0.5 mol times of at least one compound selected from hydrochloric acid, hydrobromic acid, hydroiodic acid and phosphorous acid or (B) 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst.

(6) A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of 0.005-0.5 mol times of at least one compound selected from hydrochloric acid, hydrobromic acid, hydroiodic acid and phosphorous acid per 1 mol of a rare earth atom in the rare earth oxide or rare earth hydroxide as a catalyst.

(7) A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst.

(8) A method of producing a rare earth salt of di(2-ethylhexyl) phosphate, characterized in that a rare earth oxide or a rare earth hydroxide is reacted with di(2-ethylhexyl) phosphate having a purity of not less than 97% in a non-polar solvent in the presence of at least one compound selected from a halogenated hydroacid, phosphorous acid and a rare earth halide made from the same element as in an objective product as a catalyst.

(9) A method of producing a rare earth salt of di(2-ethylhexyl) phosphate, characterized in that a rare earth oxide or a rare earth hydroxide is reacted with di(2-ethylhexyl) phosphate having a purity of not less than 97% in a non-polar solvent in the presence of (A) 0.005-0.5 mol times of at least one compound selected from a halogenated hydroacid and phosphorous acid or (B) 0.001-0.1 mol times of at least one compound selected from rare earth halides made from the same element as in an objective product per 1 mol of a rare earth atom in the rare earth oxide or rare earth hydroxide as a catalyst.

(10) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of at least one compound selected from a halogenated hydroacid, phosphorous acid and a rare earth halide made from the same element as in an objective product as a catalyst.

(11) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of (A) 0.005-0.5 mol times of at least one compound selected from a halogenated hydroacid and phosphorous acid or (B) 0.001-0.1 mol times of at least one compound selected from rare earth halides made from the same element as in an objective product per 1 mol of a rare earth atom in the rare earth oxide or rare earth hydroxide as a catalyst.

(12) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of (A) 0.005-0.5 mol times of at least one compound selected from hydrochloric acid, hydrobromic acid, hydroiodic acid and phosphorous acid or (B) 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst.

(13) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of 0.005-0.5 mol times of at least one compound selected from hydrochloric acid, hydrobromic acid, hydroiodic acid and phosphorous acid per 1 mol of a rare earth atom in the rare earth oxide or rare earth hydroxide as a catalyst.

(14) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst.

(15) A method of producing a solution of a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of at least one compound selected from a halogenated hydroacid, phosphorous acid and a rare earth halide made from the same element as in an objective product as a catalyst, and thereafter at least one metal halide selected from zinc dichloride, boron tribromide and tin tetrachloride is added.

(16) A method of producing a solution of a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of (A) 0.005-0.5 mol times of at least one compound selected from a halogenated hydroacid and phosphorous acid or (B) 0.001-0.1 mol times of at least one compound selected from rare earth halides made from the same element as in an objective product per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(17) A method of producing a solution of a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of (A) 0.005-0.5 mol times of at least one compound selected from hydrochloric acid, hydrobromic acid, hydroiodic acid and phosphorous acid or (B) 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(18) A method of producing a solution of a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of 0.005-0.5 mol times of at least one compound selected from hydrochloric acid, hydrobromic acid, hydroiodic acid and phosphorous acid per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(19) A method of producing a solution of a rare earth salt of a dialkyl phosphate or a rare earth salt of dioleyl phosphate represented by the following formula (2):

$$M[OPO(OR)_2]_3 \qquad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \qquad (1)$$

[in the formula (1), R is an alkyl group having a carbon number of 1 to 18 or oleyl group] in a non-polar solvent in the presence of 0.001-0.1 mol times of at least one compound selected from lanthanum chloride, lanthanum bromide and lanthanum iodide per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(20) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of at least one compound selected from a halogenated hydroacid, phosphorous acid and a rare earth halide made from the same element as in an objective product as a catalyst, and thereafter at least one metal halide selected from zinc dichloride, boron tribromide and tin tetrachloride is added.

(21) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of (A) 0.005-0.5 mol times of at least one compound selected from a halogenated hydroacid and phosphorous acid or (B) 0.001- 0.1 mol times of at least one compound selected from rare earth halides made from the same element as in an objective product per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(22) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of (A) 0.005-0.5 mol times of at least one compound selected from hydrochloric acid, hydrobromic acid, hydroiodic acid and phosphorous acid or (B) 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(23) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of 0.005-0.5 mol times of at least one compound selected from hydrochloric acid, hydrobromic acid, hydroiodic acid and phosphorous acid per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

(24) A method of producing a solution of a rare earth salt of di(2-ethylhexyl) phosphate in a non-polar solvent, characterized in that a rare earth oxide or a rare earth hydroxide is reacted with di(2-ethylhexyl) phosphate having a purity of not less than 97% in a non-polar solvent in the presence of 0.001-0.1 mol times of at least one compound selected from rare earth chlorides, rare earth bromides and rare earth iodides made from the same element as in an objective product per 1 mol of a rare earth atom in the rare earth oxide or rare earth hydroxide as a catalyst, and thereafter at least one metal halide selected from zinc dichloride, boron tribromide and tin tetrachloride is added at 0.005-0.5 mol times per 1 mol of the rare earth atom in the rare earth oxide or rare earth hydroxide.

As a preferable embodiment of the invention may be mentioned the above embodiments (4)-(7), (10)-(14) and (16)-(24). As a more preferable embodiment may be mentioned the embodiments (11)-(14) and (21)-(24). As a most preferable embodiment may be mentioned the embodiments (13), (14), (23) and (24). As a further preferable embodiment may be mentioned the embodiments wherein the rare earth element is lanthanum or neodymium, and as a more further preferable embodiment may be mentioned the embodiments wherein the rare earth element is lanthanum.

EXAMPLES

The following examples are given in illustration of the invention and are not intended as limitations thereof An analysis on each lanthanum dialkyl phosphate and each solution of lanthanum dialkyl phosphate in a non-polar solvent obtained in Examples and Comparative Examples is conducted by the following methods. Moreover, % in the examples and the comparative examples means mass %.

[Analysis of Lanthanum Content (%)]

It is measured by decomposing a sample with hydrochloric acid, adding an excessive amount of a solution of sodium hydroxide and then back-titrating in an EDTA solution with an XO indicator.

[Analysis of Dialkyl Phosphate Content (%) and Monoalkyl Phosphate Content (%)]

They are analyzed by decomposing a sample with hydrochloric acid, extracting dialkyl phosphate and monoalkyl phosphate with cyclohexane, adding N,O-bis(trimethylsilyl)acetamide to the extracting liquid to conduct silylation and then measuring through a gas chromatography using n-pentadecane as an internal standard.

(Measuring Conditions)

Column: capillary column (made by Agilent Technologies Inc., trade name HP-5)

Carrier gas: helium

Flow rate: 1.0 mL/min (constant pressure)

In the examples and comparative examples according to the invention, di(2-ethylhexyl) phosphate having the following composition is used as a starting material.

[Starting Material A] di(2-ethylhexyl) phosphate (97%), mono(2-ethylhexyl) phosphate (1.9%), others (1.1%)

[Starting Material B] di(2-ethylhexyl) phosphate (99%), mono(2-ethylhexyl) phosphate (0.7%), others (0.3%)

[Starting Material C] dibutyl phosphate (99%), monobutyl phosphate (0.7%), others (0.3%)

Example 1

To a four neck flask of 200 ml are added 3.26 g (10 mmol) of lanthanum oxide, 19.94 g (60 mmol) of di(2-ethylhexyl) phosphate [Starting Material A] and 100 g of cyclohexane at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 65° C. by gradually heating. Further, the reaction is continued at this temperature, and the reaction is completed at a time point that turbidity disappears and the reaction solution becomes transparent. The time from start to completion of the reaction (hereinafter referred to as reaction time) is 90 minutes. After the completion of the reaction, a reflux dehydrator is mounted onto the vessel to remove water in the reaction solution through azeotropy with cyclohexane, and then cyclohexane is distilled off under a reduced pressure to obtain 74.3 g of a solution of lanthanum di(2-ethylhexyl) phosphate in cyclohexane having a concentration of about 30%. The analytical results are shown in Table 1.

Example 2

To a four neck flask of 200 ml are added 3.26 g (10 mmol) of lanthanum oxide, 19.94 g (60 mmol) of di(2-ethylhexyl) phosphate [Starting Material A] and 95 g of cyclohexane at 20° C., and then 609 mg (2.6 mmol) of a 35% aqueous solution of phosphorous acid is added and agitated, whereby reaction is immediately started and a temperature of a reaction solution is raised up to 40° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 100 minutes. Then, the same procedure as in [Example 1] is conducted to obtain 56.6 g of a solution of lanthanum di(2-ethylhexyl) phosphate in cyclohexane having a concentration of about 40%. The analytical results are shown in Table 1.

Example 3

To a four neck flask of 200 ml are added 3.80 g (20 mmol) of lanthanum hydroxide, 19.94 g (60 mmol) of di(2-ethylhexyl) phosphate [Starting Material A] and 150 g of cyclohexane at 20° C., and then 675 mg (2.6 mmol) of 35% hydrobromic acid is added and agitated, whereby reaction is immediately started and a temperature of a reaction solution is raised up to 35° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 120 minutes. Then, the same procedure as in [Example 1] is conducted to obtain 110.2 g of lanthanum di(2-ethylhexyl) phosphate having a concentration of about 20%. The analytical results are shown in Table 1.

Comparative Example 1

To a four neck flask of 200 ml are added 19.94 g (60 mmol) of di(2-ethylhexyl) phosphate [Starting Material A] and 12.0 g (60 mmol) of a 20% aqueous solution of sodium hydroxide at 20° C., which are agitated for 60 minutes to obtain an aqueous solution of sodium di(2-ethylhexyl) phosphate. Then, 80 g of ethanol is added to this solution and subsequently 17.87 g (20 mmol) of a 26.0% aqueous solution of lanthanum chloride is added at a dropping rate of 1 ml/min, which are further reacted at the same temperature for 0 minute with stirring, whereby lanthanum di(2-ethylhexyl) phosphate is gradually precipitated to cause white turbidity in the solution. The precipitates are dissolved by adding 80 g of cyclohexane to the solution with stirring. The reaction solution is left at rest to remove the separated water layer. After the washing with 25 ml of water three times, a reflux dehydrator is mounted onto the vessel to remove water and ethanol in the reaction solution through azeotropy with cyclohexane, and then the same procedure as in [Example 1] is conducted to obtain 53.8 g of a solution of lanthanum di(2-ethylhexyl) phosphate in cyclohexane having a concentration of about 40%. The analytical results are shown in Table 1.

Comparative Example 2

To a four neck flask of 200 ml are added 19.94 g (60 mmol) of di(2-ethylhexyl) phosphate [Starting Material A] and 40.0 g of hexane at 20° C., which are gradually heated to 50° C. and thereafter 3.46 g (60 mmol) of a 29.6% aqueous solution of ammonia is added dropwise to obtain a solution of ammonium di(2-ethylhexyl) phosphate. Then, 11.8 g (20 mmol) of a 55.04% aqueous solution of lanthanum nitrate is added to this solution at a dropping rate of 1 ml/min and further the reaction is continued at the same temperature for 60 minutes. The reaction solution is left at rest to remove the separated water layer and the resulting organic phase is washed with 25 ml of water three times, and then a reflux dehydrator is mounted onto the vessel to remove water and the solvent in the reaction solution through azeotropy, and subsequently the same procedure as in [Example 1] is conducted to obtain 55.2 g of a solution of lanthanum di(2-ethylhexyl) phosphate in cyclohexane having a concentration of about 40%. The analytical results are shown in Table 1.

Comparative Example 3

To a four neck flask of 200 ml are added 3.26 g (10 mmol) of lanthanum oxide, 20.74 g (62.4 mmol) of di(2-ethylhexyl) phosphate [Starting Material A] and 70 g of cyclohexane at 20° C. and then 3.33 g (185 mmol) of water is added, which are agitated and heated to raise a temperature of a reaction solution to 45° C. Although the agitation is continued at this temperature for 4 hours, the reaction solution becomes whitely clouded. The temperature of the reaction solution is made to 70° C. by gradually heating, and further the agitation is continued at this temperature for 20 hours, but unreacted lanthanum oxide is still alive and the reaction is not completed. The reaction solution is filtered to recover 0.55 g of the unreacted lanthanum oxide. The filtrate is returned to the four neck flask and a reflux dehydrator is mounted thereonto to remove water in the filtrate through azeotropy with cyclohexane, and then the same procedure as in [Example 1] is conducted to obtain 54.5 g of a solution of lanthanum di(2-ethylhexyl) phosphate in cyclohexane having a concentration of about 40%. The analytical results are shown in Table 1.

[La]: lanthanum content
[dP]: di(2-ethylhexyl) phosphate content
[mP]: mono(2-ethylhexyl) phosphate content

TABLE 1

|  | Example | | | Comparative Example | | |
| --- | --- | --- | --- | --- | --- | --- |
|  | 1 | 2 | 3 | 1 | 2 | 3 |
| Catalyst | HCl | $H_3PO_3$ | HBr | double decomposition | double decomposition | none |
| Reaction time (minutes) | 90 | 100 | 120 | — | — | not completed in 24 hours |
| [La] (%) | 3.7 | 4.8 | 2.6 | 5.2 | 5.1 | 4.2 |
| [dP] (%) | 25.6 | 33.6 | 18.2 | 33.5 | 33.3 | 36.0 |
| [mP] (%) | 0.5 | 0.7 | 0.3 | 2.4 | 1.8 | 0.7 |
| dP/La | 2.98 | 3.01 | 3.02 | 2.78 | 2.81 | 3.69 |

In Table 1, dP/La is a molar ratio of di(2-ethylhexyl) phosphate to lanthanum in lanthanum di(2-ethylhexyl) phosphate and is calculated by an equation (3):

$$dP/La = ([dP]/322.43)/([La]/138.91) \quad (3)$$

When the value of dP/La is 3 or near to 3, di(2-ethylhexyl) phosphate and lanthanum are included at an equivalent amount or an amount near to the equivalent amount in lanthanum di(2-ethylhexyl) phosphate, which shows that the resulting lanthanum di(2-ethylhexyl) phosphate has a higher purity.

As seen from the results of Examples 1-3 and Comparative Examples 1-3, the method of the invention is superior to the conventional method. In the method through double decomposition as described in Comparative Examples, 1 and 2, however, a greater amount of mono(2-ethylhexyl) phosphate is produced by hydrolysis of di(2-ethylhexyl) phosphate, so that lanthanum di(2-ethylhexyl) phosphate with a high purity is not obtained. Also, when the catalyst is not used as described in Comparative Example 3, the reaction is not completed even in a long time, and the unreacted lanthanum oxide and di(2-ethylhexyl) phosphate remain in the completion of the reaction, and hence the unreacted di(2-ethylhexyl) phosphate is included in the solution of lanthanum di(2-ethylhexyl) phosphate in a non-polar solvent, so that lanthanum di(2-ethylhexyl) phosphate can not be obtained in a higher purity.

Example 4

To a four neck flask of 200 ml are added 3.26 g (10 mmol) of lanthanum oxide, 19.54 g (60 mmol) of di(2-ethylhexyl) phosphate [Starting Material B] and 85 g of cyclohexane at 20° C., and then 1.04 g (10 mmol) of 35% hydrochloric acid is added and agitated, whereby reaction is immediately started and a temperature of a reaction solution is raised up to 50° C. As the reaction solution becomes translucent while the reaction is continued at this temperature, the temperature of the reaction solution is raised to 60° C. by gradually heating. Further, the reaction is continued at this temperature, and the reaction is completed at a time point that turbidity disappears and the reaction solution becomes transparent. The reaction time is 30 minutes. Then, the same procedure as in [Example 1] is conducted to obtain 55.5 g of a solution of lanthanum di(2-ethylhexyl) phosphate in cyclohexane having a concentration of about 40%. The analytical results are shown in Table 2.

Example 5

To a four neck flask of 200 ml are added 3.26 g (10 mmol) of lanthanum oxide, 19.54 g (60 mmol) of di(2-ethylhexyl) phosphate [Starting Material B] and 85 g of cyclohexane at 20° C., and then 609 mg (2.6 mmol) of a 35% aqueous solution of phosphorous acid is added and agitated, whereby reaction is immediately started and a temperature of a reaction solution is raised up to 40° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 95 minutes. Then, the same procedure as in [Example 1] is conducted to obtain 54.9 g of a solution of lanthanum di(2-ethylhexyl) phosphate in cyclohexane having a concentration of about 40%. The analytical results are shown in Table 2.

Example 6

To a four neck flask of 200 ml are added 3.80 g (20 mmol) of lanthanum hydroxide, 19.54 g (60 mmol) of di(2-ethylhexyl) phosphate [Starting Material B] and 200 g of cyclohexane at 20° C., and then 675 mg (2.6 mmol) of 35% hydrobromic acid is added and agitated, whereby reaction is immediately started and a temperature of a reaction solution is raised up to 35° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 110 minutes. Then, the same procedure as in [Example 1] is conducted to obtain 73.7 g of a solution of lanthanum di(2-ethylhexyl) phosphate in cyclohexane having a concentration of about 30%. The analytical results are shown in Table 2.

Comparative Example 4

To a four neck flask of 200 ml are added 3.26 g (10 mmol) of lanthanum oxide, 20.32 g (62.4 mmol) of di(2-ethylhexyl) phosphate [Starting Material B] and 80 g of cyclohexane at 20° C., and then 3.33 g of water is added and agitated and heated to raise a temperature of a reaction solution to 50° C. Although the agitation is continued at this temperature for 4 hours, the reaction solution becomes whitely clouded. The temperature of the reaction solution is raised to 70° C. by gradually heating and further the agitation is continued at this temperature for 20 hours, but unreacted lanthanum oxide remains and the reaction is not completed. The reaction solution is filtered to recover 0.65 g of the unreacted lanthanum oxide. Then, the same procedure as in [Comparative Example 1] is conducted to obtain 53.1 g of a solution of lanthanum di(2-ethylhexyl) phosphate in cyclohexane having a concentration of about 40%. The analytical results are shown in Table 2.

Comparative Example 5

To a four neck flask of 200 ml are added 3.26 g (10 mmol) of lanthanum oxide, 19.54 g (60 mmol) of di(2-ethylhexyl) phosphate [Starting Material B] and 80 g of cyclohexane at 20° C., and then 0.41 g (2.6 mmol) of 20% nitric acid is added and agitated and heated to raise a temperature of a reaction solution to 50° C. Although the agitation is continued at this temperature for 4 hours, the reaction solution becomes whitely clouded. The temperature of the reaction solution is raised to 70° C. by gradually heating and further the agitation is continued at this temperature for 20 hours, but unreacted lanthanum oxide remains and the reaction is not completed. The reaction solution is filtered to recover 0.61 g of the unreacted lanthanum oxide. Then, the same procedure as in [Comparative Example 1] is conducted to obtain 52.8 g of a solution of lanthanum di(2-ethylhexyl) phosphate in cyclohexane having a concentration of about 40%. The analytical results are shown in Table 2.

Comparative Example 6

To a four neck flask of 200 ml are added 3.26 g (10 mmol) of lanthanum oxide, 19.54 g (60 mmol) of di(2-ethylhexyl) phosphate [Starting Material B] and 80 g of cyclohexane at 20° C., and then 2.55 g (2.6 mmol) of 10% sulfuric acid is added and agitated and heated to raise a temperature of a reaction solution to 50° C. Although the agitation is continued at this temperature for 4 hours, the reaction solution becomes whitely clouded. The temperature of the reaction solution is raised to 70° C. by gradually heating and further the agitation is continued at this temperature for 20 hours, but unreacted lanthanum oxide remains and the reaction is not completed. The reaction solution is filtered to recover 0.72 g of the unreacted lanthanum oxide. Then, the same procedure as in [Comparative Example 1] is conducted to obtain 52.5 g of a solution of lanthanum di(2-ethylhexyl) phosphate in cyclohexane having a concentration of about 40%. The analytical results are shown in Table 2.

[La]: lanthanum content
[dP]: di(2-ethylhexyl) phosphate content
[mP]: mono(2-ethylhexyl) phosphate content

TABLE 2

|  | Example | | | Comparative Example | | |
| --- | --- | --- | --- | --- | --- | --- |
|  | 4 | 5 | 6 | 4 | 5 | 6 |
| Catalyst | HCl | $H_3PO_4$ | HBr | none | $HNO_3$ | $H_2SO_4$ |
| Reaction time (minutes) | 30 | 95 | 110 | not completed in 24 hours | not completed in 24 hours | not completed in 24 hours |
| [La] (%) | 4.9 | 5.1 | 3.8 | 4.1 | 4.2 | 4.2 |
| [dP] (%) | 34.2 | 35.5 | 26.5 | 37.7 | 36.2 | 36.9 |
| [mP] (%) | 0.3 | 0.2 | 0.2 | 0.3 | 0.2 | 0.3 |
| dP/La | 3.01 | 3.00 | 3.00 | 3.96 | 3.71 | 3.79 |

The value of dP/La in Table 2 has the same meaning as in Table 1. As seen from the results of Examples 4-6 and Comparative Examples 4-6, the method of the invention is superior to the conventional method. However, when the catalyst is not used as described in Comparative Example 4, and when the catalyst other than that of the invention is used as described in Comparative Examples 5 and 6, the reaction is not completed even in a long time, and the unreacted lanthanum oxide and di(2-ethylhexyl) phosphate remain in the completion of the reaction, and hence the unreacted di(2-ethylhexyl) phosphate is included in the solution of lanthanum di(2-ethylhexyl) phosphate in a non-polar solvent, so that lanthanum di(2-ethylhexyl) phosphate can not be obtained in a higher purity.

Example 7

To a four neck flask of 200 ml are added 3.26 g (10 mmol) of lanthanum oxide, 19.94 g (60 mmol) of di(2-ethylhexyl) phosphate [Starting Material A] and 85 g of cyclohexane at 20° C., and then 11 mg (0.1 mmol) of 35% hydrochloric acid is added and agitated, whereby reaction is immediately started and a temperature of a reaction solution is raised up to 35° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 145 minutes. After the completion of the reaction, a reflux dehydrator is mounted onto the vessel to remove water in the reaction solution through azeotropy with cyclohexane, and then 52 g of cyclohexane is distilled off under a reduced pressure to obtain 55.2 g of a solution of lanthanum di(2-ethylhexyl) phosphate in cyclohexane having a concentration of about 40%. The analytical results are shown in Table 3.

Example 8

To a four neck flask of 200 ml are added 3.26 g (10 mmol) of lanthanum oxide, 19.94 g (60 mmol) of di(2-ethylhexyl) phosphate [Starting Material A] and 85 g of cyclohexane at 20° C., and then 371 mg (1 mmol) of lanthanum chloride [$LaCl_3 \cdot 7H_2O$] and 1.0 g of water are added and agitated, whereby reaction is immediately started and a temperature of a reaction solution is raised up to 50° C. As the reaction solution becomes translucent while the reaction is continued at this temperature, the temperature of the reaction solution is raised to 60° C. by gradually heating. Then, the same procedure as in [Example 7] is conducted to obtain 73.5 g of a solution of lanthanum di(2-ethylhexyl) phosphate in cyclohexane having a concentration of about 30%. The analytical results are shown in Table 3.

Example 9

To a four neck flask of 200 ml are added 3.26 g (10 mmol) of lanthanum oxide, 19.94 g (60 mmol) of di(2-ethylhexyl) phosphate [Starting Material A] and 400 g of cyclohexane at 20° C., and then 470 mg (2.6 mmol) of 10% hydrochloric acid is added and agitated, whereby reaction is immediately started and a temperature of a reaction solution is raised up to 35° C. As the reaction solution becomes translucent while the reaction is continued at this temperature, the temperature of the reaction solution is raised to 65° C. by gradually heating. Then, the same procedure as in [Example 7] is conducted to obtain 110.8 g of a solution of lanthanum di(2-ethylhexyl) phosphate in cyclohexane having a concentration of about 20%. The analytical results are shown in Table 3.

Example 10

To a four neck flask of 200 ml are added 3.26 g (10 mmol) of lanthanum oxide, 19.94 g (60 mmol) of di(2-ethylhexyl) phosphate [Starting Material A] and 40 g of cyclohexane at 20° C., and then 31.6 g (2.6 mmol) of 0.3% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 60° C. by gradually heating. Further, the reaction is continued at this temperature, and the reaction is completed at a time point that turbidity disappears and the reaction solution becomes transparent. After the reaction solution is left at rest to remove the separated water layer, the same procedure as in [Example 1] is conducted to obtain 55.5 g of a solution of lanthanum di(2-ethylhexyl) phosphate in cyclohexane having a concentration of about 40%. The analytical results are shown in Table 3.

Comparative Example 7

To a four neck flask of 200 ml are added 3.26 g (10 mmol) of lanthanum oxide, 19.94 g (60 mmol) of di(2-ethylhexyl) phosphate [Starting Material A] and 85 g of cyclohexane at 20° C. and then 3.33 g of water is added, which are agitated and heated to raise a temperature of a reaction solution to 50° C. Although the agitation is continued at this temperature for 4 hours, the reaction solution becomes whitely clouded. The temperature of the reaction solution is made to 70° C. by gradually heating, and further the agitation is continued at this temperature for 20 hours, but unreacted lanthanum oxide is still alive and the reaction is not completed. The reaction solution is filtered to recover 0.85 g of the unreacted lanthanum oxide. The filtrate is returned to the four neck flask and a reflux dehydrator is mounted thereonto to remove water in the filtrate through azeotropy with cyclohexane to obtain a solution of lanthanum di(2-ethylhexyl) phosphate in hexane. Further, hexane is distilled off under a reduced pressure to obtain 53.5 g of a solution of lanthanum di(2-ethylhexyl) phosphate in hexane having a concentration of about 40%. The analytical results are shown in Table 3.

[La]: lanthanum content
[dP]: di(2-ethylhexyl) phosphate content
[mP]: mono(2-ethylhexyl) phosphate content

TABLE 3

| | Example | | | | Comparative Example |
|---|---|---|---|---|---|
| | 7 | 8 | 9 | 10 | 7 |
| Catalyst | HCl | $LaCl_3$ | HCl | HCl | none |
| Reaction time (minutes) | 145 | 60 | 100 | 50 | not completed in 24 hours |
| [La] (%) | 5.0 | 3.8 | 2.5 | 5.2 | 3.9 |
| [dP] (%) | 34.5 | 26.3 | 17.2 | 36.1 | 36.5 |
| [mP] (%) | 0.7 | 0.5 | 0.4 | 0.7 | 0.5 |
| dP/La | 2.97 | 2.98 | 2.96 | 2.99 | 4.03 |

The value of dP/La in Table 3 has the same meaning as in Table 1. Moreover, the lanthanum content in Example 8 is obtained by subtracting the lanthanum amount in lanthanum chloride used as a catalyst from the actually analytical value. As seen from the results of Examples 7-10 and Comparative Example 7, the method of the invention is superior to the conventional method. When the catalyst is not used as described in Comparative Example 7, the reaction is not completed even in a long time, and the unreacted lanthanum oxide and di(2-ethylhexyl) phosphate remain in the completion of the reaction, and hence the unreacted di(2-ethylhexyl) phosphate is included in the solution of lanthanum di(2-ethylhexyl) phosphate in a non-polar solvent, so that lanthanum di(2-ethylhexyl) phosphate can not be obtained in a higher purity.

Example 11

To a four neck flask of 200 ml are added 3.26 g (10 mmol) of lanthanum oxide, 19.54 g (60 mmol) of di(2-ethylhexyl) phosphate [Starting Material B] and 150 g of cyclohexane at 20° C., and then 213 mg (2.6 mmol) of phosphorous acid and 0.4 g of water are added and agitated, whereby reaction is immediately started and a temperature of a reaction solution is raised up to 40° C. As the reaction solution becomes translucent while the reaction is continued at this temperature, the temperature of the reaction solution is raised to 70° C. by gradually heating. Then, the same procedure as in [Example 7] is conducted to obtain 75.2 g of a solution of lanthanum di(2-ethylhexyl) phosphate in cyclohexane having a concentration of about 30%. The analytical results are shown in Table 4.

Example 12

To a four neck flask of 200 ml are added 3.26 g (10 mmol) of lanthanum oxide, 19.54 g (60 mmol) of di(2-ethylhexyl)

phosphate [Starting Material B] and 200 g of cyclohexane at 20° C., and then 33 mg (0.2 mmol) of a 50% aqueous solution of phosphorous acid is added and agitated, whereby reaction is immediately started and a temperature of a reaction solution is raised up to 30° C. As the reaction solution becomes translucent while the reaction is continued at this temperature, the temperature of the reaction solution is raised to 70° C. by gradually heating. Then, the same procedure as in [Example 7] is conducted to obtain 109.5 g of a solution of lanthanum di(2-ethylhexyl) phosphate in cyclohexane having a concentration of about 20%. The analytical results are shown in Table 4.

Example 13

To a four neck flask of 200 ml are added 3.26 g (10 mmol) of lanthanum oxide, 19.54 g (60 mmol) of di(2-ethylhexyl) phosphate [Starting Material B] and 85 g of cyclohexane at 20° C., and then 820 mg (5 mmol) of a 50% aqueous solution of phosphorous acid is added and agitated, whereby reaction is immediately started and a temperature of a reaction solution is raised up to 45° C. As the reaction solution becomes translucent while the reaction is continued at this temperature, the temperature of the reaction solution is raised to 70° C. by gradually heating. Then, the same procedure as in [Example 7] is conducted to obtain 54.7 g of a solution of lanthanum di(2-ethylhexyl) phosphate in cyclohexane having a concentration of about 40%. The analytical results are shown in Table 4.

Example 14

To a four neck flask of 200 ml are added 3.26 g (10 mmol) of lanthanum oxide, 19.74 g (60.6 mmol) of di(2-ethylhexyl) phosphate [Starting Material B] and 120 g of hexane at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 60° C. by gradually heating. Then, the same procedure as in [Example 7] is conducted to obtain 74.0 g of a solution of lanthanum di(2-ethylhexyl) phosphate in hexane having a concentration of about 30%. The analytical results are shown in Table 4.

Example 15

To a four neck flask of 200 ml are added 3.26 g (10 mmol) of lanthanum oxide, 19.93 g (61.2 mmol) of di(2-ethylhexyl) phosphate [Starting Material B] and 120 g of toluene at 20° C., and then 760 mg (2 mmol) of lanthanum bromide [$LaBr_3$] and 3.04 g of water are added and agitated, whereby reaction is immediately started and a temperature of a reaction solution is raised up to 45° C. As the reaction solution becomes translucent while the reaction is continued at this temperature, the temperature of the reaction solution is raised to 70° C. by gradually heating. Then, the same procedure as in [Example 7] is conducted to obtain 111.2 g of a solution of lanthanum di(2-ethylhexyl) phosphate in toluene having a concentration of about 20%. The analytical results are shown in Table 4.

Example 16

To a four neck flask of 200 ml are added 3.26 g (10 mmol) of lanthanum oxide, 19.54 g (60 mmol) of di(2-ethylhexyl) phosphate [Starting Material B] and 85 g of hexane at 0° C., and then 270 mg (2.6 mmol) of 35% hydrochloric acid is added and agitated, whereby reaction is immediately started and a temperature of a reaction solution is raised up to 25° C. As the reaction solution becomes translucent while the reaction is continued at this temperature, the temperature of the reaction solution is raised to 60° C. by gradually heating. Then, the same procedure as in [Example 7] is conducted to obtain 54.3 g of a solution of lanthanum di(2-ethylhexyl) phosphate in hexane/toluene having a concentration of about 40%. The analytical results are shown in Table 4.

Example 17

To a four neck flask of 200 ml are added 3.26 g (10 mmol) of lanthanum oxide, 19.54 g (60 mmol) of di(2-ethylhexyl) phosphate [Starting Material B] and 85 g of toluene at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 80° C. by gradually heating. Then, the same procedure as in [Example 7] is conducted to obtain 72.8 g of a solution of lanthanum di(2-ethylhexyl) phosphate in hexane/toluene having a concentration of about 30%. The analytical results are shown in Table 4.

Example 18

To a four neck flask of 200 ml are added 3.26 g (10 mmol) of lanthanum oxide, 19.54 g (60 mmol) of di(2-ethylhexyl) phosphate [Starting Material B], 50 g of hexane and 50 g of cyclohexane at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 60° C. by gradually heating. Then, the same procedure as in [Example 7] is conducted to obtain 56.4 g of a solution of lanthanum di(2-ethylhexyl) phosphate in hexane/cyclohexane having a concentration of about 40%. The analytical results are shown in Table 4.

Comparative Example 8

To a four neck flask of 200 ml are added 3.26 g (10 mmol) of lanthanum oxide, 20.32 g (62.4 mmol) of di(2-ethylhexyl) phosphate [Starting Material B] and 150 g of toluene at 20° C. and then 3.33 g of water is added, which are agitated and heated to raise a temperature of a reaction solution to 50° C. Although the agitation is continued at this temperature for 4 hours, the reaction solution becomes whitely clouded. The temperature of the reaction solution is made to 80° C. by gradually heating, and further the agitation is continued at this temperature for 20 hours, but unreacted lanthanum oxide is still alive and the reaction is not completed. The reaction solution is filtered to recover 0.68 g of the unreacted lanthanum oxide. Then, the same procedure as in [Comparative Example 5] is conducted to obtain 52.8 g of a solution of lanthanum di(2-ethylhexyl) phosphate in toluene having a concentration of about 40%. The analytical results are shown in Table 4.

[La]: lanthanum content
[dP]: di(2-ethylhexyl) phosphate content
[mP]: mono(2-ethylhexyl) phosphate content

TABLE 4

|  | Example | | | | | | | | Comparative Example |
|---|---|---|---|---|---|---|---|---|---|
|  | 11 | 12 | 13 | 14 | 15 | 16 | 17 | 18 | 8 |
| Catalyst | $H_3PO_3$ | $H_3PO_3$ | $H_3PO_3$ | HCl | $LaBr_3$ | HCl | HCl | HCl | none |
| Reaction time (minutes) | 115 | 180 | 65 | 90 | 80 | 100 | 60 | 95 | not completed in 24 hours |
| [La] (%) | 3.8 | 2.5 | 5.0 | 3.7 | 2.5 | 5.0 | 3.7 | 5.0 | 4.2 |
| [dP] (%) | 26.2 | 17.4 | 34.8 | 26.0 | 17.7 | 34.8 | 26.0 | 34.8 | 37.8 |
| [mP] (%) | 0.2 | 0.1 | 0.3 | 0.3 | 0.2 | 0.3 | 0.2 | 0.2 | 0.4 |
| dP/La | 2.97 | 3.00 | 3.00 | 3.03 | 3.05 | 3.00 | 3.03 | 3.00 | 3.88 |

The value of dP/La in Table 4 has the same meanings as in Table 1. Moreover, the lanthanum content in Example 15 is obtained by subtracting the lanthanum amount in lanthanum bromide used as a catalyst from the actually analytical value. As seen from the results of Examples 11-18 and Comparative Example 8, the method of the invention is superior to the conventional method. When the catalyst is not used as described in Comparative Example 8, the reaction is not completed even in a long time, and the unreacted lanthanum oxide and di(2-ethylhexyl) phosphate remain in the completion of the reaction, and hence the unreacted di(2-ethylhexyl) phosphate is included in the solution of lanthanum di(2-ethylhexyl) phosphate in a non-polar solvent, so that lanthanum di(2-ethylhexyl) phosphate can not be obtained in a higher purity.

Example 19

To a four neck flask of 200 ml are added 3.26 g (10 mmol) of lanthanum oxide, 12.74 g (60 mmol) of dibutyl phosphate [Starting Material C] and 85 g of cyclohexane at 20° C., and then 609 mg (2.6 mmol) of a 35% aqueous solution of phosphorous acid is added and agitated, whereby reaction is immediately started and a temperature of a reaction solution is raised up to 40° C. As the reaction solution becomes translucent while the reaction is continued at this temperature, the temperature of the reaction solution is raised to 70° C. by gradually heating. Then, the same procedure as in [Example 7] is conducted to obtain 38.3 g of a solution of lanthanum dibutyl phosphate in cyclohexane having a concentration of about 40%. The analytical results are shown in Table 5.

Example 20

To a four neck flask of 200 ml are added 3.80 g (20 mmol) of lanthanum hydroxide, 12.74 g (60 mmol) of dibutyl phosphate [Starting Material C] and 170 g of cyclohexane at 20° C., and then 675 mg (2.6 mmol) of a 35% aqueous solution of hydrobromic acid is added and agitated, whereby reaction is immediately started and a temperature of a reaction solution is raised up to 35° C. As the reaction solution becomes translucent while the reaction is continued at this temperature, the temperature of the reaction solution is raised to 70° C. by gradually heating. Then, the same procedure as in [Example 7] is conducted to obtain 76.9 g of a solution of lanthanum dibutyl phosphate in cyclohexane having a concentration of about 20%. The analytical results are shown in Table 5.

Example 21

To a four neck flask of 200 ml are added 3.26 g (10 mmol) of lanthanum oxide, 12.74 g (60 mmol) of dibutyl phosphate [Starting Material C] and 150 g of cyclohexane at 20° C., and then 213 mg (2.6 mmol) of phosphorous acid and 0.4 g of water are added and agitated, whereby reaction is immediately started and a temperature of a reaction solution is raised up to 40° C. As the reaction solution becomes translucent while the reaction is continued at this temperature, the temperature of the reaction solution is raised to 70° C. by gradually heating. Then, the same procedure as in [Example 7] is conducted to obtain 77.1 g of a solution of lanthanum dibutyl phosphate in cyclohexane having a concentration of about 20%. The analytical results are shown in Table 5.

Example 22

To a four neck flask of 200 ml are added 3.26 g (10 mmol) of lanthanum oxide, 12.74 g (61.2 mmol) of dibutyl phosphate [Starting Material C] and 85 g of cyclohexane at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 65° C. by gradually heating. Then, the same procedure as in [Example 7] is conducted to obtain 51.5 g of a solution of lanthanum dibutyl phosphate in cyclohexane having a concentration of about 30%. The analytical results are shown in Table 5.

Example 23

To a four neck flask of 200 ml are added 3.26 g (10 mmol) of lanthanum oxide, 12.74 g (60 mmol) of dibutyl phosphate [Starting Material C] and 120 g of toluene at 20° C., and then 270 mg (2.6 mmol) of 35% hydrochloric acid is added and agitated, whereby reaction is immediately started and a temperature of a reaction solution is raised up to 40° C. As the reaction solution becomes translucent while the reaction is continued at this temperature, the temperature of the reaction solution is raised to 75° C. by gradually heating. Then, the same procedure as in [Example 7] is conducted to obtain 39.8 g of a solution of lanthanum dibutyl phosphate in toluene having a concentration of about 40%. The analytical results are shown in Table 5.

Example 24

To a four neck flask of 200 ml are added 3.26 g (10 mmol) of lanthanum oxide, 12.74 g (60 mmol) of dibutyl phosphate [Starting Material C] and 85 g of cyclohexane at 20° C., and then 49 mg (0.02 mmol) of a 10% aqueous solution of lanthanum chloride is added and agitated, whereby reaction is immediately started and a temperature of a reaction solution is raised up to 45° C. As the reaction solution becomes translucent while the reaction is continued at this temperature, the temperature of the reaction solution is raised to 65° C. by gradually heating. Then, the same procedure as in [Example 7] is conducted to obtain 50.7 g of a solution of lanthanum dibutyl phosphate in cyclohexane having a concentration of about 30%. The analytical results are shown in Table 5.

Comparative Example 9

To a four neck flask of 200 ml are added 3.26 g (10 mmol) of lanthanum oxide, 12.74 g (60 mmol) of dibutyl phosphate [Starting Material C] and 100 g of cyclohexane at 20° C. and then 3.33 g of water is added, which are agitated and heated to raise a temperature of a reaction solution to 50° C. Although the agitation is continued at this temperature for 4 hours, the reaction solution becomes whitely clouded. The temperature of the reaction solution is made to 70° C. by gradually heating, and further the agitation is continued at this temperature for 20 hours, but unreacted lanthanum oxide is still alive and the reaction is not completed. The reaction solution is filtered to recover 0.58 g of the unreacted lanthanum oxide. Then, the same procedure as in [Comparative Example 5] is conducted to obtain 75.7 g of a solution of lanthanum dibutyl phosphate in cyclohexane having a concentration of about 20%. The analytical results are shown in Table 5.

[La]: lanthanum content
[dP]: dibutyl phosphate content
[mP]: monobutyl phosphate content

TABLE 5

| | Example | | | | | | Comparative Example |
|---|---|---|---|---|---|---|---|
| | 19 | 20 | 21 | 22 | 23 | 24 | 9 |
| Catalyst | $H_3PO_3$ | HBr | $H_3PO_3$ | HCl | HCl | $LaCl_3$ | none |
| Reaction time (minutes) | 70 | 90 | 85 | 100 | 80 | 90 | not completed in 24 hours |
| [La] (%) | 7.2 | 3.6 | 3.5 | 5.4 | 7.0 | 5.4 | 3.1 |
| [dP] (%) | 32.5 | 16.4 | 15.9 | 24.9 | 31.7 | 24.5 | 26.7 |
| [mP] (%) | 0.2 | 0.1 | 0.1 | 0.2 | 0.3 | 0.2 | 0.1 |
| dP/La | 2.98 | 3.01 | 3.00 | 3.02 | 2.99 | 3.00 | 3.71 |

In Table 5, dP/La is a molar ratio of dibutyl phosphate to lanthanum in lanthanum dibutyl phosphate and is calculated by the following equation (4):

$$dP/La = ([dP]/210.21)/([La]/138.91) \quad (4)$$

When the value of dP/La is 3 or near to 3, dibutyl phosphate and lanthanum are included at an equivalent amount or an amount near to the equivalent amount in lanthanum dibutyl phosphate, which shows that the resulting lanthanum dibutyl phosphate has a higher purity. Moreover, the lanthanum content in Example 24 is obtained by subtracting the lanthanum amount in lanthanum chloride used as a catalyst from the actually analytical value. As seen from the results of Examples 19-24 and Comparative Example 9, the method of the invention is superior to the conventional method. When the catalyst is not used as described in Comparative Example 9, the reaction is not completed even in a long time, and the unreacted lanthanum oxide and dibutyl phosphate remain in the completion of the reaction, and hence the unreacted dibutyl phosphate is included in the solution of lanthanum dibutyl phosphate in a non-polar solvent, so that lanthanum dibutyl phosphate can not be obtained in a higher purity.

Example 25

To a four neck flask of 200 ml are added 3.26 g (10 mmol) of lanthanum oxide, 19.54 g (60 mmol) of di(2-ethylhexyl) phosphate [Starting Material B] and 100 g of cyclohexane at 20° C., and then 270 mg (2.6 mmol) of 35% hydrochloric acid is added and agitated, whereby reaction is immediately started and a temperature of a reaction solution is raised up to 45° C. As the reaction solution becomes translucent while the reaction is continued at this temperature, the temperature of the reaction solution is raised to 65° C. by gradually heating. Further, the reaction is continued at this temperature, and the reaction is completed at a time point that turbidity disappears and the reaction solution becomes transparent. The reaction time is 90 minutes. The viscosity of the reaction solution is 800 cp. The reaction solution is added and agitated with 0.26 g (1 mmol) of tin tetrachloride, and a reflux dehydrator is mounted to remove water in the reaction solution through azeotropy with the solvent and then cyclohexane is distilled off under a reduced pressure to obtain 111.2 g of a solution of lanthanum di(2-ethylhexyl) phosphate in cyclohexane having a concentration of 20%. The viscosity of this solution is 65 cp. The analytical results are shown in Table 6.

Example 26

To a four neck flask of 200 ml are added 3.26 g (10 mmol) of lanthanum oxide, 19.54 g (60 mmol) of di(2-ethylhexyl) phosphate [Starting Material B] and 85 g of cyclohexane at 20° C., and then 609 mg (2.6 mmol) of a 35% aqueous solution of phosphorous acid is added and agitated, whereby reaction is immediately started and a temperature of a reaction solution is raised up to 45° C. As the reaction solution becomes translucent while the reaction is continued at this temperature, the temperature of the reaction solution is raised to 70° C. by gradually heating. Further, the reaction is continued at this temperature, and the reaction is completed at a time point that turbidity disappears and the reaction solution becomes transparent. The reaction time is 100 minutes. Then, a reflux dehydrator is mounted to remove water in the reaction solution through azeotropy with the solvent and then cyclohexane is distilled off under a reduced pressure to obtain 73.8 g of a solution of lanthanum di(2-ethylhexyl) phosphate in cyclohexane having a concentration of 30%. The viscosity of this solution is 2000 cp. When this solution is added and agitated with 0.26 g (1 mmol) of tin tetrachloride, the viscosity is lowered to 85 cp. The analytical results are shown in Table 6.

Example 27

To a four neck flask of 200 ml are added 3.80 g (20 mmol) of lanthanum hydroxide, 19.54 g (60 mmol) of di(2-ethylhexyl) phosphate [Starting Material B] and 200 g of hexane at 20° C., and then 675 mg (2.6 mmol) of 35% hydrobromic acid is added and agitated, whereby reaction is immediately started and a temperature of a reaction solution is raised up to 35° C. As the reaction solution becomes translucent while the reaction is continued at this temperature, the temperature of the reaction solution is raised to 60° C. by gradually heating. Further, the reaction is continued at this temperature, and the reaction is completed at a time point that turbidity disappears and the reaction solution becomes transparent. The reaction time is 120 minutes. The viscosity of the reaction solution is 600 cp. The reaction solution is added and agitated with 0.26 g (1 mmol) of tin tetrachloride, and a reflux dehydrator is mounted to remove water in the reaction solution through azeotropy with the solvent and then cyclohexane is distilled off under a reduced pressure to obtain 108.8 g of a solution of lanthanum di(2-ethylhexyl) phosphate in cyclohexane having a concentration of 20%. The viscosity of this solution is 60 cp. The analytical results are shown in Table 6.

[La]: lanthanum content
[dP]: di(2-ethylhexyl) phosphate content
[mP]: mono(2-ethylhexyl) phosphate content

TABLE 6

|  | Example | | |
|---|---|---|---|
|  | 25 | 26 | 27 |
| Catalyst | HCl | H₃PO₃ | HBr |
| Reaction time (minutes) | 90 | 100 | 110 |
| [La] (%) | 2.5 | 3.7 | 2.6 |
| [dP] (%) | 17.3 | 25.9 | 18.0 |
| [mP] (%) | 0.1 | 0.2 | 0.1 |
| dP/La | 2.98 | 3.02 | 2.98 |
| Lewis acid | SnCl₄ | SnCl₄ | SnCl₄ |
| Viscosity (cp) | 65 | 80 | 60 |

The value of dP/La in Table 6 has the same meanings as in Table 1. As seen from the results of Examples 25-27, when Lewis acid is added after the reaction using the catalyst according to the invention, lanthanum di(2-ethylhexyl) phosphate of a high purity is obtained as a non-polar solvent solution having an extremely lowered viscosity as compared with the case using no Lewis acid.

INDUSTRIAL APPLICABILITY

According to the invention, there can be produced rare earth salt of dialkyl phosphate and rare earth salt of dioleyl phosphate, which can be used as a component of a composite catalyst usable as a polymerization catalyst of a conjugated diene compound, in a higher purity.

The invention claimed is:

1. A method of producing a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group], characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of at least one compound selected from a halogenated hydroacid, phosphorous acid and a rare earth halide as a catalyst.

2. The method according to claim 1, wherein the rare earth element is neodymium, lanthanum, scandium, yttrium, samarium or gadolinium.

3. The method according to claim 2, wherein the rare earth element is neodymium or lanthanum.

4. The method according to claim 3, wherein the rare earth element is lanthanum.

5. The method according to claim 1, wherein the dialkyl phosphate is di(2-ethylhexyl) phosphate, and the rare earth salt of dialkyl phosphate is a rare earth salt of di(2-ethylhexyl) phosphate.

6. The method according to claim 1, wherein the halogenated hydroacid is selected from hydrochloric acid, hydrobromic acid and hydroiodic acid.

7. The method according to claim 1, wherein the rare earth element of the rare earth halide and the rare earth element of the rare earth oxide or rare earth hydroxide are the same rare earth element or different rare earth elements.

8. The method according to claim 7, wherein the rare earth element of the rare earth halide and the rare earth element of the rare earth oxide or rare earth hydroxide are the same rare earth element.

9. The method according to claim 1, wherein the halogen of the rare earth halide is chlorine.

10. A method of producing a solution of a rare earth salt of a dialkyl phosphate or a rare earth salt of dioleyl phosphate represented by the following formula (2):

$$M[OPO(OR)_2]_3 \quad (2)$$

[in the formula (2), M is a rare earth element and R is an alkyl group having a carbon number of 1 to 18 or oleyl group] in a non-polar solvent, characterized in that a rare earth oxide or a rare earth hydroxide is reacted with a dialkyl phosphate or dioleyl phosphate having a purity of not less than 97% and represented by the following formula (1):

$$HOPO(OR)_2 \quad (1)$$

[in the formula (1), R is an alkyl group having a carbon number of 1 to 18 or oleyl group] in a non-polar solvent in the presence of at least one compound selected from a halogenated hydroacid, phosphorous acid and a rare earth halide as a catalyst, and thereafter at least one metal halide selected from zinc dichloride, boron tribromide and tin tetrachloride is added.

11. The method according to claim 10, wherein the rare earth element is neodymium, lanthanum, scandium, yttrium, samarium or gadolinium.

12. The method according to claim 11, wherein the rare earth element is neodymium or lanthanum.

13. The method according to claim 12, wherein the rare earth element is lanthanum.

14. The method according to claim 10, wherein the dialkyl phosphate is di(2-ethylhexyl) phosphate, and the rare earth salt of dialkyl phosphate is a rare earth salt of di(2-ethylhexyl) phosphate.

15. The method according to claim 10, wherein the halogenated hydroacid is selected from hydrochloric acid, hydrobromic acid and hydroiodic acid.

16. The method according to claim 10, wherein the rare earth element of the rare earth halide and the rare earth element of the rare earth oxide or rare earth hydroxide are the same rare earth element or different rare earth elements.

17. The method according to claim 16, wherein the rare earth element of the rare earth halide and the rare earth element of the rare earth oxide or rare earth hydroxide are the same rare earth element.

18. The method according to claim 10, wherein the halogen of the rare earth halide is chlorine.

* * * * *